United States Patent [19]

Holton

[11] Patent Number: 5,015,744
[45] Date of Patent: May 14, 1991

[54] METHOD FOR PREPARATION OF TAXOL USING AN OXAZINONE

[75] Inventor: Robert A. Holton, Tallahassee, Fla.

[73] Assignee: Florida State University, Tallahassee, Fla.

[21] Appl. No.: 436,235

[22] Filed: Nov. 14, 1989

[51] Int. Cl.$^5$ .................. C07D 305/00; C07D 303/00
[52] U.S. Cl. ..................... 549/510; 549/214;
549/215; 549/332; 549/511; 549/512; 549/513;
549/539; 560/27; 560/29; 560/32; 560/160;
560/162
[58] Field of Search ............ 549/510, 511, 214, 215,
549/332, 512, 513, 539; 560/27, 29, 32, 160, 162

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,924,011 | 5/1990 | Denis et al. | 549/510 |
| 4,924,012 | 5/1990 | Colin et al. | 549/510 |

FOREIGN PATENT DOCUMENTS

| | | | |
|---|---|---|---|
| 253738 | 1/1988 | European Pat. Off. | 549/511 |
| 253739 | 1/1988 | European Pat. Off. | 549/510 |
| 336840 | 10/1989 | European Pat. Off. | 549/510 |
| 336841 | 10/1989 | European Pat. Off. | 549/510 |

OTHER PUBLICATIONS

March, Advanced Org. Chem. 3rd Edition, p. 351, Reaction 0-25, Alcoholysis of Esters.
Katritzky, "Handbook of Heterocyclic Chemistry", Pergamon Press, p. 173.
Wani et al., "Plant Antitumor Agents. VI. The Isolation and Structure of Taxol, a Novel Antileukemic and Antitumor Agent from *Taxus brevifolia*", J. Am. Chem. Soc. 93:9, May 5, 1971, pp. 2325-2327.
Holton, "Synthesis of the Taxane Ring System", J. Am. Chem. Soc., 1984, 106, pp. 5731-5732.
Denis et al., "A Highly Efficient, Practical Approach to Natural Taxol", J. Am. Chem. Soc. 1988, 110, 5917-5919.
Holton et al., "A Synthesis of Taxusin", J. Am. Chem. Soc., 1988, 110, pp. 6558-6560.

*Primary Examiner*—Cecilia Shen
*Attorney, Agent, or Firm*—Senniger, Powers, Leavitt & Roedel

[57] ABSTRACT

Process for the preparation of a taxol intermediate comprising contacting an alcohol with an oxazinone having the formula:

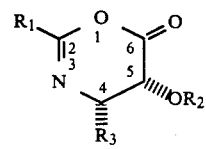

wherein $R_1$ is aryl, substituted aryl, alkyl, alkenyl, or alkynyl; $R_2$ is hydrogen, ethoxyethyl, 2,2,2-trichloroethoxymethyl or other hydroxyl protecting group; and $R_3$ is aryl, substituted aryl, alkyl, alkenyl, or alkynyl; the contacting of said alcohol and oxazinone being carried out in the presence of a sufficient amount of an activating agent under effective conditions to cause the oxazinone to react with the alcohol to form a $\beta$-amido ester which is suitable for use as an intermediate in the synthesis of taxol.

19 Claims, No Drawings

METHOD FOR PREPARATION OF TAXOL USING AN OXAZINONE

This invention was made with Government support under NIH Grant #CA 42031 awarded by the National Institute of Health. The Government has certain rights in the invention.

BACKGROUND OF THE INVENTION

The present invention is directed to a novel oxazinone, a process for its preparation, and a process for the preparation of taxol involving the use of such oxazinone.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity, having the following structure:

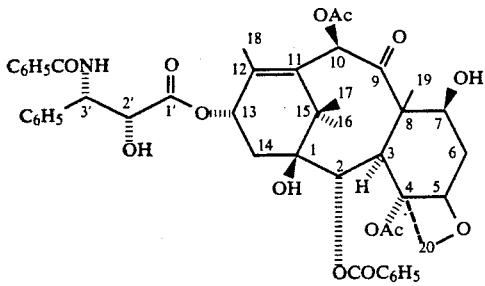

Because of this promising activity, taxol is currently undergoing clinical trials in both France and the United States.

The supply of taxol for these clinical trials is presently being provided by the bark from several species of yew. However, taxol is found only in minute quantities in the bark of these slow growinq evergreens, causing considerable concern that the limited supply of taxol will not meet the demand. Consequently, chemists in recent years have expended their energies in trying to find a viable synthetic route for the preparation of taxols. So far, the results have not been entirely satisfactory.

One synthetic route that has been proposed is directed to the synthesis of the tetracyclic taxane nucleus from commodity chemicals. A synthesis of the taxol congener taxusin has been reported by Holton, et al. in JACS 110, 6558 (1988). Despite the progress made in this approach, the final total synthesis of taxol is, nevertheless, likely to be a multi-step, tedious, and costly process.

An alternate approach to the preparation of taxol has been described by Greene, et al in JACS 110, 5917 (1988), and involves the use of a congener of taxol, 10-deacetyl baccatin III which has the structure shown below:

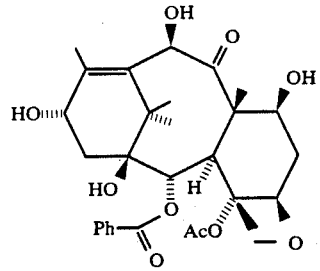

10-deacetyl baccatin III is more readily available than taxol since it can be obtained from the leaves of *Taxus baccata*. According to the method of Greene et al., 10-deacetyl baccatin III is converted to taxol by attachment of the C10 acetyl group and by attachment of the C13 β-amido ester side chain through the esterification of the C-13 alcohol with a B-amido carboxylic acid unit. Although this approach requires relatively few steps, the synthesis of the β-amido carboxylic acid unit is a multi-step process which proceeds in low yield, and the coupling reaction is tedious and also proceeds in low yield. However, this coupling reaction is a key step which is required in every contemplated synthesis of taxol or biologically active derivative of taxol, since it has been shown by Wani, et al. in JACS 93, 2325 (1971) that the presence of the β-amido ester side chain at C13 is required for anti-tumor activity.

A major difficulty remaining in the synthesis of taxol and other potential anti-tumor agents is the lack of a readily available unit which could be easily attached to the C13 oxygen to provide the β-amido ester side chain. Development of such a unit and a process for its attachment in high yield would facilitate the synthesis of taxol as well as related anti-tumor agents having a modified set of nuclear substituents or a modified C13 side chain. This need has been fulfilled by the discovery of a new, readily available, side chain precursor chemical unit and an efficient process for its attachment at the C13 oxygen.

SUMMARY OF THE INVENTION

Among the objects of the present invention, therefore, is the provision of a side chain precursor for the synthesis of taxols, and the provision of a process for the attachment of the side chain precursor in relatively high yield to provide a taxol intermediate.

Briefly, therefore, the present invention is directed to a side chain precursor, an oxazinone 1 of the formula:

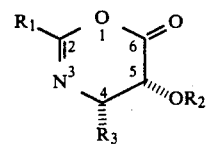

wherein $R_1$ is aryl, substituted aryl, alkyl, alkenyl, or alkynyl; $R_2$ is hydrogen, ethoxyethyl, acetal, or other hydroxyl protecting group; and $R_3$ is aryl, substituted aryl, alkyl, alkenyl, or alkynyl.

The present invention is also directed to a process for the preparation of a taxol intermediate comprising contacting an alcohol with an oxazinone 1 in the presence of a sufficient amount of an activating agent under effective conditions to cause the oxazinone to react with the alcohol to form a β-amido ester which may be used as an intermediate in the synthesis of taxol.

The present invention is also directed to a process for the preparation of taxol which comprises contacting an alcohol with oxazinone 1 in the presence of a sufficient amount of an activating agent under effective conditions to cause the oxazinone to react with the alcohol to form a β-amido ester taxol intermediate. The intermediate is then used in the synthesis of taxol.

Other objects and features of this invention will be in part apparent and in part pointed out hereinafter.

DETAILED DESCRIPTION

The present invention is directed to an oxazinone 1 and its derivatives, the structure of which is depicted hereinbelow.

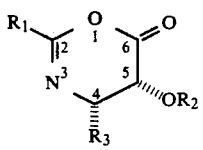

As noted above, $R_1$ is aryl, substituted aryl, alkenyl, or alkynyl; $R_2$ is hydrogen, ethoxyethyl, acetal or other hydroxyl protecting group; and $R_3$ is aryl, substituted aryl, alkyl, alkenyl, or alkynyl. Preferably, $R_1$ is phenyl, substituted phenyl, or aryl; $R_2$ is ethoxyethyl, 2,2,2-trichloroethoxymethyl, or other acetal hydroxyl protecting group; and $R_3$ is phenyl, substituted phenyl, or aryl. The structure of the preferred oxazinone in which $R_1$ and $R_3$ are phenyl and $R_2$ is ethoxyethyl is shown below:

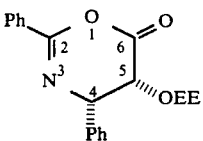

According to IUPAC rules, the name of oxazinone 2 is 2,4-diphenyl-5-(1-ethoxyethoxy)-4,5-dihydro-1,3-oxazin-6-one.

In accordance with the present invention, a process is provided for preparing taxol intermediates, natural taxol and non-naturally occurring taxols having the following structural formula:

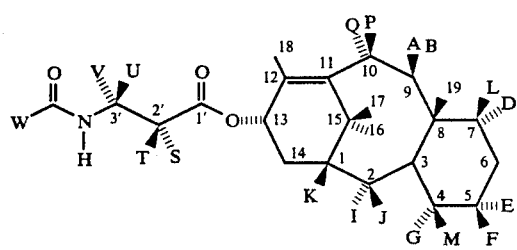

wherein
A and B are independently hydrogen or lower alkanoyloxy, alkenoyloxy, alkynoyloxy, or aryloyloxy or
A and B together form an oxo;

L and D are independently hydrogen or hydroxy or lower alkanoyloxy, alkenoyloxy, alkynoyloxy, or aryloyloxy;

E and F are independently hydrogen or lower alkanoyloxy, alkenoyloxy, alkynoyloxy, or aryloyloxy or;

E and F together form an oxo;

G is hydrogen or hydroxy or lower alkanoyloxy, alkenoyloxy, alkynoyloxy, or aryloyloxy or G and M together form an oxo or methylene or G and M together form an oxirane or M and F together form an oxetane;

J is hydrogen, hydroxy, or lower alkanoyloxy, alkenoyloxy, alkynoyloxy, or aryloyloxy or I is hydrogen, hydroxy, or lower alkanoyloxy, alkenoyloxy, alkynoyloxy, or aryloyloxy; or I and J taken together form an oxo; and K is hydrogen, hydroxy or lower alkoxy, alkanoyloxy, alkenoyloxy, alkynoyloxy, or aryloyloxy; and P and Q are independently hydrogen or lower alkanoyloxy, alkenoyloxy, alkynoyloxy, or aryloyloxy or P and Q together form an oxo; and S and T are independently hydrogen or lower alkanoyloxy, alkenoyloxy, alkynoyloxy, or aryloyloxy or S and T together form an oxo; and U and V are independently hydrogen or lower alkyl, alkenyl, alkynyl, aryl, or substituted aryl; and W is aryl, substituted aryl, lower alkyl, alkenyl, or alkynyl.

The taxol alkyl groups, either alone or with the various substituents defined hereinabove are preferably lower alkyl containing from one to six carbon atoms in the principal chain and up to 10 carbon atoms. They may be straight or branched chain and include methyl, ethyl, propyl, isopropyl, butyl, isobutyl, tert-butyl, aryl, hexyl, and the like.

The taxol alkenyl groups, either alone or with the various substituents defined hereinabove are preferably lower alkenyl containing from two to six carbon atoms in the principal chain and up to 10 carbon atoms. They may be straight or branched chain and include ethenyl, propenyl, isopropenyl, butenyl, isobutenyl, aryl, hexenyl, and the like.

The taxol alkynyl groups, either alone or with the various substituents defined hereinabove are preferably lower alkynyl containing from two to six carbon atoms in the principal chain and up to 10 carbon atoms. They may be straight or branched chain and include ethynyl, propynyl, butynyl, isobutynyl, aryl, hexynyl, and the like.

Exemplary alkanoyloxy include acetate, propionate, butyrate, valarate, isobutyrate and the like. The more preferred alkanoyloxy is acetate.

The taxol aryl moieties, either alone or with various substituents contain from 6 to 10 carbon atoms and include phenyl, α-naphthyl or β-naphthyl, etc. Substituents include alkanoxy, hydroxy, halogen, alkyl, aryl, alkenyl, acyl, acyloxy, nitro, amino, amido, etc. Phenyl is the more preferred aryl.

As defined herein, the term "aryloyloxy" includes aromatic heterocyclic moieties.

Preferred values of the substituents A, B, D, L, E, F, G, M, I, J, K, P, Q, S, T, U, V, and W are enumerated below in Table I.

TABLE I

| | | | | | |
|---|---|---|---|---|---|
| A and B together, form an oxo | A=H B=OAc, | A=OCOR B=H, | A=B=H; | | |
| L=H | L=OH | L=D=H; | | | |
| D=OH, | D=H, | | | | |
| E=H, | E=OAc, | E and F together form an oxo, | E=H F=O (oxetane); | | |
| F=OAc, | F=H | | | | |
| G and M=CH$_2$, | G=CH$_2$ M=O (epoxide) | G=O M=CH$_2$ (epoxide), | G and M together form an oxo, | G=OAc M=CH$_2$O (oxetane) | G=H M=CH$_2$O (oxetane) |
| I=J=O, | I=J=H | I—COPh J=H; | I=COAr J=H; | | |
| K=H, | K=OH, | K=OR, | K—OCOR, | K=OCOAr, | |
| P and Q together, form an oxo | P=H Q=OAc, | P=OCOR Q=H, | P=Q=H; | | |
| S and T together, form an oxo | S=H T—OCOR, | S=H T=OR, | S=OCOR T=H, | S=OR T=H, | S=OH T=H, S=H T=OH; |
| U=H | U=H | U=H | U=Ph | U=Ar | U=R U=V=H; |
| V=R, | V=Ph, | V=Ar, | V=H, | V=H, | V=H, |
| W=R, | W=Ph, | W=Ar; | | | |

Exemplary compounds within the generic formula are depicted hereinbelow:

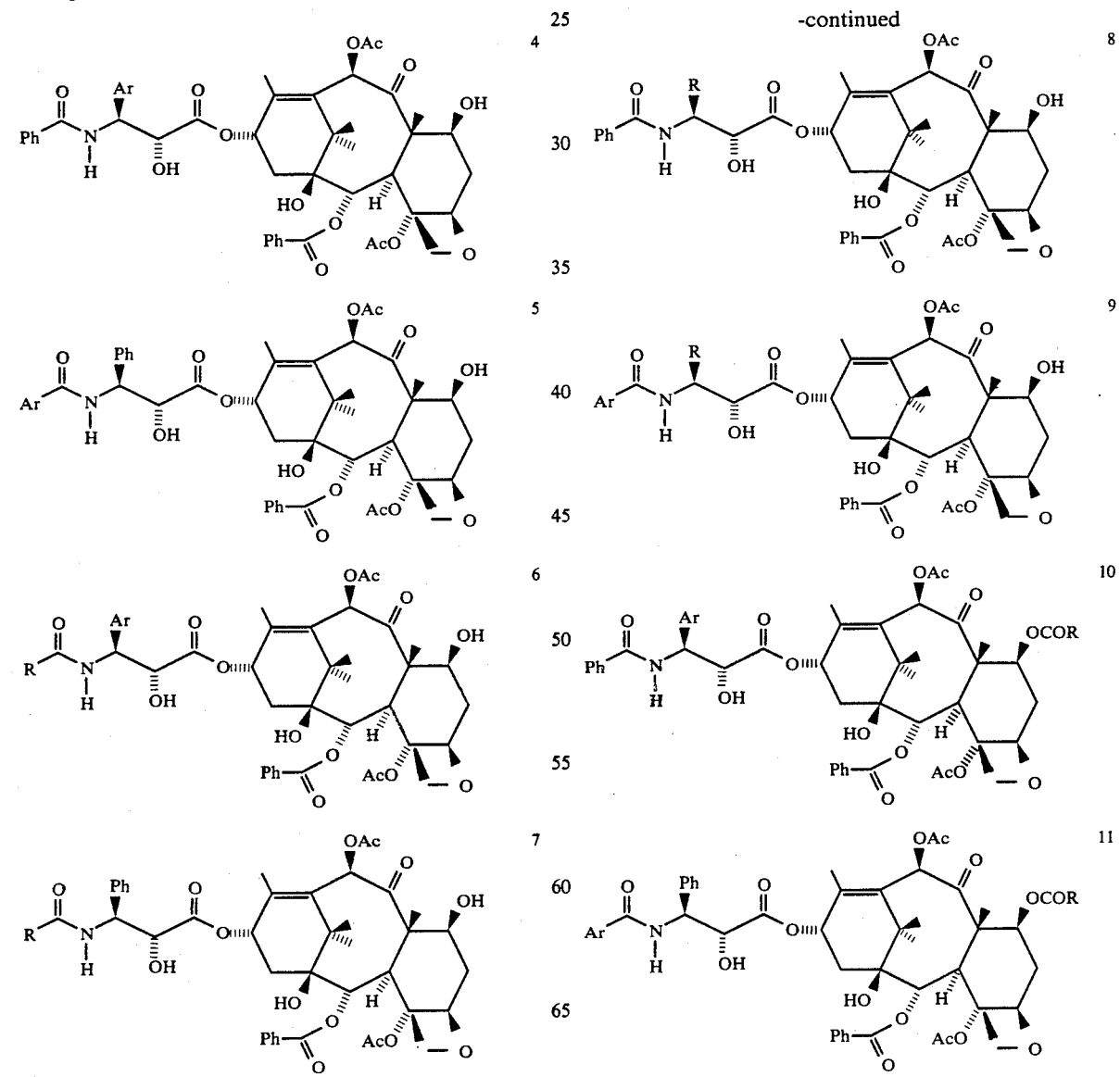

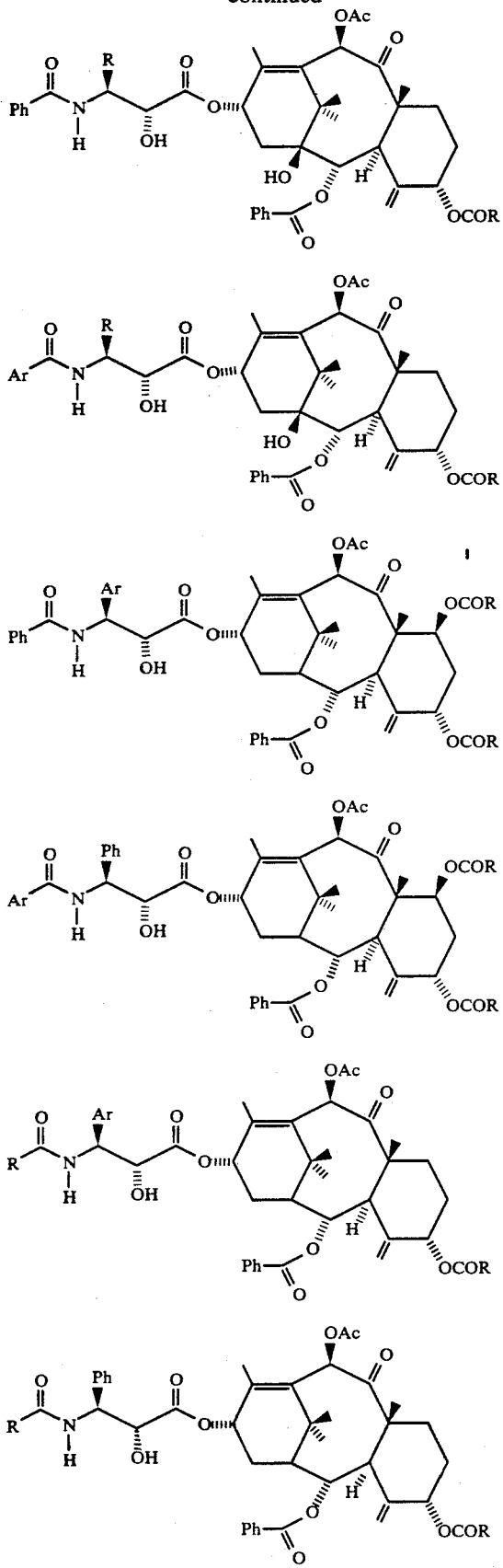

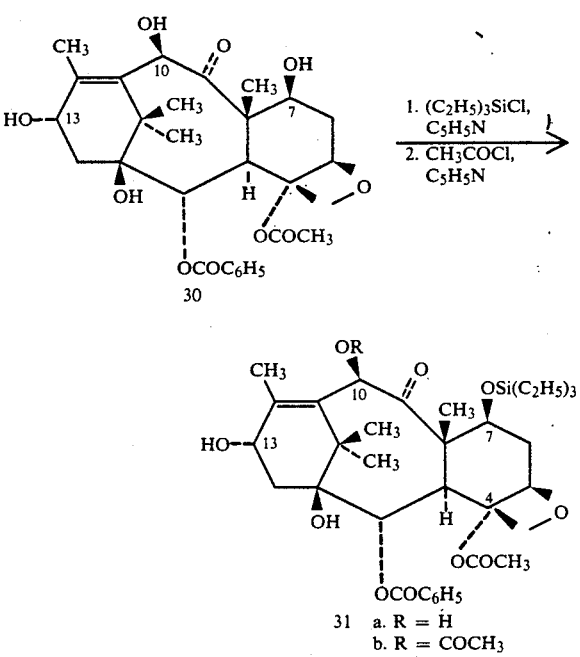

preferably a tertiary amine such as triethyl amine, diisopropyl ethyl amine, pyridine, N-methyl imidazole, and 4-dimethylaminopyridine (DMAP). For example, oxazinones 1 react with compounds having the taxane tetracyclic nucleus and a C13 hydroxyl group, in the presence of 4-dimethylaminopyridine (DMAP), to provide substances having a β-amido ester group at C13.

Most preferably, the alcohol is 7-O-triethylsilyl baccatin III which can be obtained as described by Greene, et al. in JACS 110, 5917 (1988) or by other routes. As reported in Greene et al., 10-deacetyl baccatin III is converted to 7-O-triethylsilyl baccatin III according to the following reaction scheme:

Under what is reported to be carefully optimized conditions, 10-deacetyl baccatin III is reacted with 20 equivalents of $(C_2H_5)_3SiCl$ at 23° C. under an argon atmosphere for 20 hours in the presence of 50 mL of pyridine/mmol of 10-deacetyl baccatin III to provide 7-triethylsilyl-10-deacetyl baccatin III (31a) as a reaction product in 84–86% yield after purification. The reaction product is then acetylated with 5 equivalents of $CH_3COCl$ and 25 mL of pyridine/mmol of 31a at 0° C. under an argon atmosphere for 48 hours to provide 86% yield of 7-O-triethylsilyl baccatin III (31b). Greene, et al. in JACS 110, 5917 at 5918 (1988).

As shown in the following reaction scheme, 7-O-triethylsilyl baccatin III 31b may be reacted with an oxazinone of the present invention at room temperature to provide a taxol intermediate in which the C-7 and C-2' hydroxyl groups are protected with triethylsilyl and ethoxyethyl protecting groups, respectively. These groups are then hydrolyzed under mild conditions so as not to disturb the ester linkage or the taxol substituents. The synthesis of taxol from oxazinone 2 is carried out as follows:

In accordance with the process of the present invention, oxazinones 1 are converted to β-amido esters in the presence of an alcohol and an activating agent,

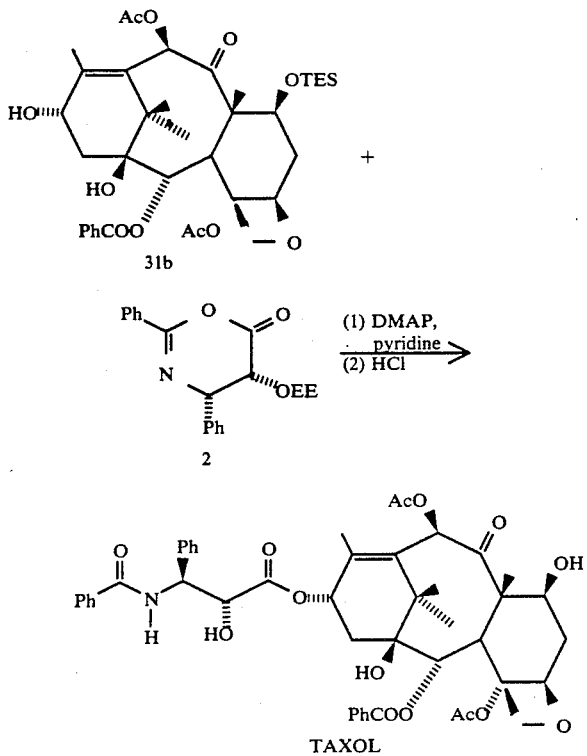

TAXOL

| $R_1$ = Ph | $R_1$ = Ar | $R_1$ = p-MeOPh | $R_1$ = alkyl | $R_1$ = alkenyl | $R_1$ = alkynyl | $R_1$ = H |
|---|---|---|---|---|---|---|
| $R_2$ = EE | $R_2$ = SiR$_3$ | $R_2$ = alkyl | $R_2$ = OCOR | $R_2$ = MOM | $R_2$ = Cl$_3$CCH$_2$OCH$_2$ | |
| $R_3$ = Ph | $R_3$ = Ar | $R_3$ = p-MeOPh | $R_3$ = alkyl | $R_3$ = alkenyl | $R_3$ = alkynyl | $R_3$ = H |

Although the present scheme is directed to the synthesis of the natural product taxol, it can be used with modifications in either the oxazinone or the tetracyclic alcohol, which can be derived from natural or unnatural sources, to prepare other synthetic taxols contemplated within the present invention.

Alternatively, an oxazinone 1 may be converted to a β-amido ester in the presence of an activating agent and an alcohol other than 7-O-triethylsilyl baccatin III to form a taxol intermediate. Synthesis of taxol may then proceed using the taxol intermediate under an appropriate reaction scheme.

The oxazinone alkyl groups, either alone or with the various substituents defined hereinabove are preferably lower alkyl containing from one to six carbon atoms in the principal chain and up to 15 carbon atoms. They may be straight or branched chain and include methyl, ethyl, propyl, isopropyl, butyl, isobutyl, tert-butyl, aryl, hexyl, and the like.

The oxazinone alkenyl groups, either alone or with the various substituents defined hereinabove are preferably lower alkenyl containing from two to six carbon atoms in the principal chain and up to 15 carbon atoms. They may be straight or branched chain and include ethenyl, propenyl, isopropenyl, butenyl, isobutenyl, aryl, hexenyl, and the like.

The oxazinone alkynyl groups, either alone or with the various substituents defined hereinabove are preferably lower alkynyl containing from two to six carbon atoms in the principal chain and up to 15 carbon atoms. They may be straight or branched chain and include ethynyl, propynyl, butynyl, isobutynyl, aryl, hexynyl, and the like.

Exemplary oxazinone alkanoyloxy include acetate, propionate, butyrate, valarate, isobutyrate and the like. The more preferred alkanoyloxy is acetate.

The oxazinone aryl moieties described, either alone or with various substituents contain from 6 to 15 carbon atoms and include phenyl, α-naphthyl or β-naphthyl, etc. Substituents include alkanoxy, hydroxy, halogen, alkyl, aryl, alkenyl, acyl, acyloxy, nitro, amino, amido, etc. Phenyl is the more preferred aryl.

As noted above, $R_2$ of oxazinone 1 may be alkyl, acyl, ethoxyethyl, 2,2,2-trichloroethoxymethyl, or other hydroxyl protecting group such as acetals and ethers, i.e., methoxymethyl, benzyloxymethyl; esters, such as acetates; carbonates, such as methyl carbonates; and the like. A variety of protecting groups for the hydroxyl group and the synthesis thereof may be found in "Protective Groups in Organic Synthesis" by T. W. Greene, John Wiley and Sons, 1981. The hydroxyl protecting group selected should be easily removed under conditions that are sufficiently mild so as not to disturb the ester linkage or other substituents of the taxol intermediate. However, $R_2$ is preferably ethoxyethyl or 2,2,2-trichloroethoxymethyl, and most preferably ethoxyethyl.

Preferred values of the oxazinone substituents $R_1$, $R_2$, and $R_3$ are enumerated herein below:

Since the oxazinone 1 has several asymmetric carbons, it is known to those skilled in the art that the compounds of the present invention having asymmetric carbon atoms may exist in diastereomeric, racemic, or optically active forms. All of these forms are contemplated within the scope of this invention. More specifically, the present invention includes enantiomers, diastereomers, racemic mixtures, and other mixtures thereof.

The oxazinones 1 can be prepared from readily available materials according to the following reaction scheme:

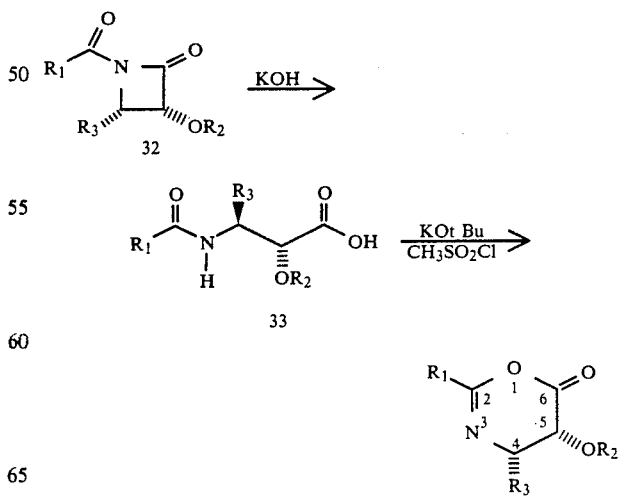

Carboxylic acid 33 may alternatively be prepared according to the method described in Greene et al., JACS 110, 5917 (1988). β-lactams 32 can be prepared from readily available materials, as illustrated in the following reaction scheme in which $R_1$ and $R_3$ are phenyl and $R_2$ is ethoxyethyl:

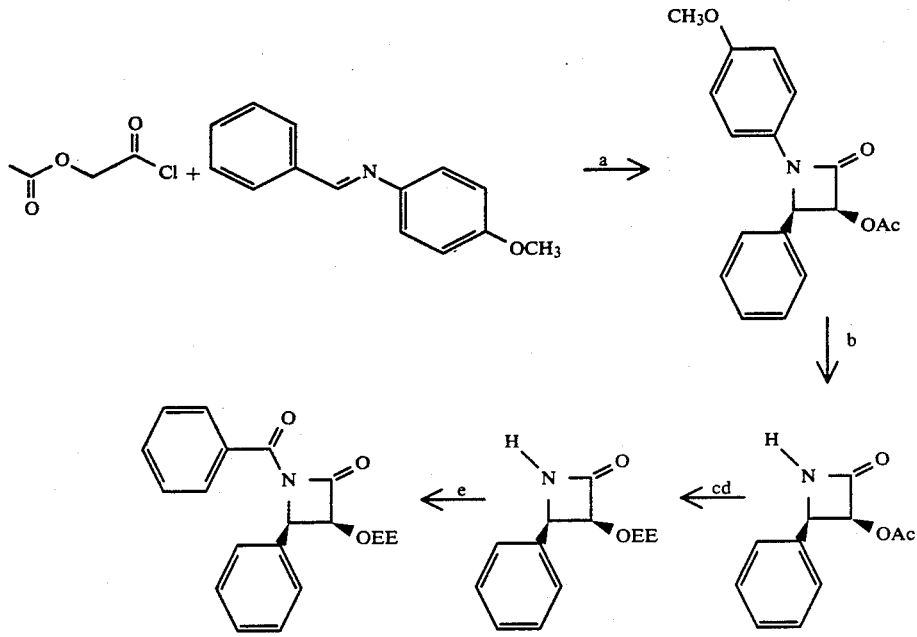

reagents: (a) triethylamine, $CH_2Cl_2$, 25° C., 18 h; (b) 4 equiv ceric ammonium nitrate, $CH_3CN$, −10° C., 10 min; (c) KOH, THF, $H_2O$, 0° C., 30 min; (d) ethyl vinyl ether, THF, toluene sulfonic acid (cat.), 0° C., 1.5h; (e) $CH_3Li$, ether, −78° C., 10 min; benzoyl chloride, −78° C., 1h.

The starting materials are readily available. α-Acyloxy acetyl chloride is prepared from glycolic acid, and, in the presence of a tertiary amine, it cyclocondenses with imines prepared from aldehydes and p-methoxyaniline to give 1-p-methoxyphenyl-3-acyloxy-4-arylazetidin-2-ones.

The p-methoxyphenyl group can be readily removed through oxidation with ceric ammonium nitrate, and the acyloxy group can be hydrolyzed under standard conditions familiar to those experienced in the art to provide 3-hydroxy-4-arylazetidin-2-ones.

The 3-hydroxyl group may be protected with a variety of standard protecting groups such as the 1-ethoxyethyl group. Preferably, the racemic 3-hydroxy-4-arylazetidin-2-one is resolved into the pure enantiomers prior to protection by recrystallization of the corresponding 2-methoxy-2-(trifluoromethyl) phenylacetic esters and only the dextrorotatory enantiomer is used in the preparation of taxol. In any event, the 3-(1-ethoxyethoxy)-4-phenylazetidin-2-one can be converted to β-lactam 32, by treatment with a base, preferably n-butyllithium, and an aroyl chloride at −78° C. or below.

The following examples illustrate the invention.

EXAMPLE 1

Preparation of
Cis-2,4-diphenyl-5-(1-Ethoxyethoxy)-4,5-Dihydro-1,3-Oxazin-6-One 2 cis-1-p-methoxyphenyl-3-acetoxy-4-phenylazetidin-2-one. To a solution of 962 mg (4.56 mmol) of the imine derived from benzaldehyde and p-methoxy aniline, and 0.85 mL (6.07 mmol) of triethylamine in 15 mL of $CH_2Cl_2$ at −20° C. was added dropwise a solution of 412 mg (3.04 mmol) of α-acetoxy acetyl chloride in 15 mL of $CH_2Cl_2$. The reaction mixture was allowed to warm to 25° C. over an 18 h period. The reaction mixture was then diluted with 100 mL of $CH_2Cl_2$ and the solution was extracted with 30 mL of 10% aqueous HCl. The organic layer was washed with 30 mL of water and 30 mL of saturated aqueous sodium bicarbonate, dried over sodium sulfate, and concentrated to provide a solid mass. The solid was triturated with 50 mL of hexane and the mixture was filtered. The remaining solid was recrystallized from ethyl acetate/hexane to give 645 mg (68%) of cis-1-p-methoxyphenyl-3-acetoxy-4-phenylazetidin-2-one as white crystals, m.p. 163° C.

cis-3-acetoxy-4-phenylazetidin-2-one. To a solution of 20.2 g of cis-1-p-methoxyphenyl-3-acetoxy-4-phenylazetidin-2-one in 700 mL of acetonitrile at −10° C. was slowly added a solution of ceric ammonium nitrate in 450 mL of water over a 1 h period. The mixture was stirred for 30 min at −10° C. and diluted with 500 mL of ether. The aqueous layer was extracted with two 100 mL portions of ether, and the combined organic layer was washed with two 100 mL portions of water, two 100 mL portions of saturated aqueous sodium bisulfite, two 100 mL portions of saturated aqueous sodium bicarbonate and concentrated to give 18.5 g of a solid. Recrystallization of the solid from acetone/hexane gave 12.3 g (92%) of cis-3-acetoxy-4-phenylazetidin-2-one as white crystals, m.p. 152°-154° C.

cis 3 hydroxy 4 phenylazetidin 2 one. To a mixture of 200 mL of THF and 280 mL of 1M aqueous potassium hydroxide solution at 0° C. was added a solution of 4.59 g (22.4 mmol) of cis-3-acetoxy-4-phenylazetidin-2-one in 265 mL of THF via a dropping funnel over a 40 min period. The solution was stirred at 0° C. for 1 h and 100 mL of water and 100 mL of saturated sodium bicarbonate were added. The mixture was extracted with four 200 mL portions of ethyl acetate and the combined organic layers were dried over sodium sulfate and concentrated to give 3.54 g (97%) of racemic cis-3-hydroxy-4-phenylazetidin-2-one as white crystals, m.p. 147°-149° C. This material was resolved into its enantiomers by recrystallization of its 2-methoxy-2-(trifluoromethyl)phenylacetic ester from hexane/acetone followed by hydrolysis, $[\alpha]^{25}_{Hg}$ 177°.

cis-3-(1-ethoxyethoxy)-4-phenylazetidin 2-one. To a solution of 3.41 g (20.9 mmol) of cis-3-hydroxy-4-phenylazetidin-2-one in 15 mL of THF at 0° C. was added 5 mL of ethyl vinyl ether and 20 mg (0.2 mmol) of methane-sulfonic acid. The mixture was stirred at 0° C. for 20 min, diluted with 20 mL of saturated aqueous sodium bicarbonate, and extracted with three 40 mL portions of ethyl acetate. The combined ethyl acetate layers were dried over sodium sulfate and concentrated to give 4.87 g (99%) of cis-3-(1-ethoxyethoxy)-4-phenylazetidin-2-one as a colorless oil.

cis-1-benzoyl-3-(1-ethoxyethoxy)-4-phenylazetidin-2-one. To a solution of 2.35 g (10 mmol) of cis-3-(1-ethoxyethoxy)-4-phenylazetidin-2-one in 40 mL of THF at −78° C. was added 6.1 mL (10.07 mmol) of a 1.65M solution of n-butyllithium in hexane. The mixture was stirred for 10 min at −78° C. and a solution of 1.42 g (10.1 mmol) of benzoyl chloride in 10 mL of THF was added. The mixture was stirred at −78° C. for 1 h and diluted with 70 mL of saturated aqueous sodium bicarbonate and extracted with three 50 mL portions of ethyl acetate. The combined ethyl acetate extracts were dried over sodium sulfate and concentrated to give 3.45 g of an oil. Chromatography of the oil on silica gel eluted with ethyl acetate/hexane gave 3.22 g (95%) of cis-1-benzoyl-3-(1-ethoxyethoxy)-4-phenylazetidin-2-one as a colorless oil.

2R,3S-N-benzoyl-O-(1-ethoxyethyl)-3-phenylisoserine. To a solution of 460 mg (1.36 mmol) of cis-1-benzoyl-3-(1-ethoxyethoxy)-4-phenylazetidin-2-one in 20 mL of THF at 0° C. was added 13.5 mL of a 1M aqueous solution (13.5 mmol) of potassium hydroxide. The mixture was stirred at 0° C. for 10 min and the THF was evaporated. The mixture was partitioned between 12 mL of a 1N aqueous HCl solution and 30 mL of chloroform. The aqueous layer was extracted with two additional 30 mL portions of chloroform. The combined chloroform extracts were dried over sodium sulfate and concentrated to provide 416 mg (86%) of 2R,3S-N-benzoyl-O-(1-ethoxyethyl)-3-phenylisoserine (formula 33 in which $R_1$ and $R_3$ are phenyl and $R_2$ is ethoxyethyl).

cis-2,4-diphenyl-5-(1-ethoxyethoxy)-4,5-dihydro-1,3-oxazin-6-one 2. To a solution of 416 mg (1.16 mmol) of 2R,3S-N-benzoyl-O-(1-ethoxyethyl)-3-phenylisoserine in 20 mL of THF was added 261 mg (2.33 mmol) of solid potassium tert-butoxide and the mixture was stirred at 25° C. for 30 min. A solution of 134 mg (1.16 mmol) of methanesulfonyl chloride in 3.2 mL of THF was added and the mixture was stirred at 25° C. for 1.5 h. The mixture was diluted with 80 mL of hexane and ethyl acetate and this solution was extracted with 20 mL of saturated aqueous sodium bicarbonate solution and 10 mL of brine. The organic phase was dried over sodium sulfate and concentrated to give 256 mg (65%) of cis-2,4-diphenyl-5-(1-ethoxyethoxy)-4,5-dihydro-1,3-oxazin-6-one 2 as a colorless oil, $[\alpha]^{25}_{Hg}$ −22° (CHCl$_3$, c 1.55).

EXAMPLE 2

Preparation of Taxol

To a small reaction vessel was added 77 mg (0.218 mmol) of (−)-cis-2,4-diphenyl-5-(1-ethoxyethoxy)-4,5-dihydro-1,3-oxazin-6-one 2, 40 mg (0.057 mmol) of 7-O-triethylsilyl baccatin III, 6.9 mg (0.057 mmol) of 4-dimethylamino pyridine (DMAP), and 0.029 mL of pyridine. The mixture was stirred at 25° C. for 12 h and diluted with 100 mL of ethyl acetate. The ethyl acetate solution was extracted with 20 mL of 10% aqueous copper sulfate solution, dried over sodium sulfate and concentrated. The residue was filtered through a plug of silica gel eluted with ethyl acetate. Flash chromatography on silica gel eluted with ethyl acetate/hexane followed by recrystallization from ethyl acetate/hexane gave 46 mg (77%) of 2'-O-(1-ethoxyethyl)-7-O-triethylsilyl taxol as a ca. 2:1 mixture of diastereomers and 9.3 mg (23%) of 7-O-triethylsilyl baccatin III. The yield based on consumed 7-O-triethylsilyl baccatin III was quantitative.

A 5 mg sample of 2'-(1-ethoxyethoxy)-7-O-triethylsilyl taxol was dissolved in 2 mL of ethanol and 0.5 mL of 0.5% aqueous HCl solution was added. The mixture was stirred at 0° C. for 30 h and diluted with 50 mL of ethyl acetate. The solution was extracted with 20 mL of saturated aqueous sodium bicarbonate solution, dried over sodium sulfate and concentrated. The residue was purified by column chromatography on silica gel eluted with ethyl acetate/hexane to provide 3.8 mg (ca. 90%) of taxol, which was identical with an authentic sample in all respects.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What is claimed is:

1. A process for the preparation of a taxol having the formula:

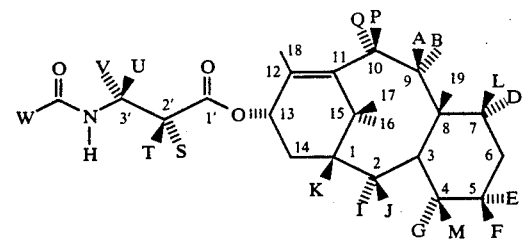

wherein
- A and B are independently hydrogen or lower alkanoyloxy, alkenoyloxy, alkynoyloxy, or aryloyloxy or
- A and B together form an oxo;
- L and D are independently hydrogen or hydroxy or lower alkanoyloxy, alkenoyloxy, alkynoyloxy, or aryloyloxy;
- E and F are independently hydrogen or lower alkanoyloxy, alkenoyloxy, alkynoyloxy, or aryloyloxy or;
- E and F together from an oxo;
- G is hydrogen or hydroxy or lower alkanoyloxy, alkenoyloxy, alkynoyloxy, or aryloyloxy or G and M together form an oxo or methylene or
G and M together form an oxirane or
M and F together form an oxetane;
J is hydrogen, hydroxy, or lower alkanoyloxy, alkenoyloxy, alkynoyloxy, or aryloyloxy or
I is hydrogen, hydroxy, or lower alkanoyloxy, alkenoyloxy, alkynoyloxy, or aryloyloxy; or
I and J taken together form an oxo; and
K is hydrogen, hydroxy or lower alkoxy, alkanoyloxy, alkenoyloxy, alkynoyloxy, or aryloyloxy; and
P and Q are independently hydrogen or lower alkanoyloxy, alkenoyloxy, alkynoyloxy, or aryloyloxy or
P and Q together form an oxo; and
S and T are independently hydrogen or lower alkanoyloxy, alkenoyloxy, alkynoyloxy, or aryloyloxy or
S and T together form an oxo; and
U and V are independently hydrogen or lower alkyl, alkenyl, alkynyl, aryl, or substituted aryl; and
W is aryl, substituted aryl, lower alkyl, alkenyl, or alkynyl,
comprising:
contacting an oxazinone of the formula:

wherein $R_1$ is aryl, substituted aryl, alkyl, alkenyl, or alkynyl; $R_2$ is hydrogen, ethoxyethyl, 2,2,2-trichloroethoxymethyl or other hydroxyl protecting group; and $R_3$ is aryl, substituted aryl, alkyl, alkenyl, or alkynyl; with an alcohol of the formula:

wherein said A, B, D, E, F, G, I, J, K, L, M, P and Q are as defined above, the contacting of said oxazinone and said alcohol being carried out in the presence of a sufficient amount of an activating agent to cause the oxazinone to react with the alcohol to form a β-amido ester which is suitable for use as an intermediate in the synthesis of taxol, and converting said intermediate to taxol.

2. The process of claim 1 wherein aryl is $C_{6-15}$ aryl, substituted aryl is $C_{6-15}$ substituted aryl, the substituents of which are selected from alkanoxy, hydroxy, halogen, alkyl, aryl, alkenyl, acyl, acyloxy, nitro, amino, and amido, alkyl is $C_{1-15}$ alkyl, alkenyl is $C_{2-15}$ alkenyl and alkynyl is $C_{2-15}$ alkynyl, alkanoyloxy is $C_{1-15}$ alkanoyloxy, alkenoyloxy is $C_{2-15}$ alkenoyloxy, alkynoyloxy is $C_{2-15}$ alkynoyloxy, and aryloyloxy is $C_{6-15}$ aryloyloxy.

3. The process of claim 1 wherein said alcohol has the following formula:

wherein $R_4$ is a hydroxyl protecting group.

4. The process of claim 3 wherein $R_4$ is selected from ethers, esters, carbonates and silyl groups.

5. The process of claim 3 wherein $R_4$ is ethoxyethyl, trimethyl silyl or triethyl silyl.

6. The process of claim 3 wherein said $R_1$ is phenyl and said $R_3$ is phenyl.

7. The process of claim 6 wherein said activating agent is triethyl amine, diisopropyl ethyl amine, pyridine, N-methyl imidazole, or 4-dimethylaminopyridine.

8. The process of claim 1 wherein said other hydroxyl protecting group is selected from ethers, esters, carbonates and silyl groups.

9. The process of claim 1 where said activating agent is a tertiary amine.

10. The process of claim 1 wherein said activating agent is triethyl amine, diisopropyl ethyl amine, pyridine, N-methyl imidazole, or 4-dimethylaminopyridine.

11. The process of claim 1 wherein $R_1$ is phenyl.

12. The process of claim 1 wherein $R_1$ and $R_3$ are phenyl.

13. The process of claim 12 wherein $R_4$ is ethoxyethyl.

14. The process of claim 1 wherein $R_2$ is ethoxyethyl.

15. A process for the preparation of taxol comprising reacting an oxazinone of the formula wherein $R_2$ is a hydroxyl protecting group and Ph is phenyl, with an alcohol of the formula wherein $R_4$ is a hydroxyl protecting group, in the presence of a tertiary amine activating agent to form an intermediate, and converting the intermediate to taxol by hydrolyzing the $R_2$ and $R_4$ hydroxyl protecting groups.

16. The process of claim 15 wherein $R_2$ and $R_4$ are independently selected from ethers, esters, carbonates and silyl groups.

17. The process of claim 15 wherein $R_2$ and $R_4$ are independently selected from ethoxyethyl, trimethyl silyl or triethyl silyl.

18. The process of claim 15 wherein the tertiary amine activating agent is triethyl amine, diisopropyl ethyl amine, pyridine, N-methyl imidazole, or 4-dimethylaminopyridine.

19. The process of claim 15 wherein said reacting step is carried out at a temperature of 25° C.

* * * * *